(12) United States Patent
Li et al.

(10) Patent No.: US 8,002,409 B2
(45) Date of Patent: Aug. 23, 2011

(54) VISION TREATMENT PROCEDURES AND DEVICES

(75) Inventors: Geng Li, Heng Fa Chuen (HK);
Zhong-Lin Lu, Irvine, CA (US);
Xiangrui Li, Alhambra, CA (US);
Chang-Bing Huang, Alhambra, CA (US); Jia-Hong Gao, Chicago, IL (US);
Yeung-Ming Chow, Tai Po (HK)

(73) Assignee: Hon Kong Applied Science and Technology Research Institute Co., Ltd., Hong Kong (CN)

( * ) Notice: Subject to any disclaimer, the term of this patent is extended or adjusted under 35 U.S.C. 154(b) by 92 days.

(21) Appl. No.: 12/502,517

(22) Filed: Jul. 14, 2009

(65) Prior Publication Data

US 2011/0013138 A1 Jan. 20, 2011

(51) Int. Cl.
*A61B 3/00* (2006.01)
*A61B 3/02* (2006.01)

(52) U.S. Cl. .......................... 351/203; 351/222
(58) Field of Classification Search ............ 351/222, 351/223, 237, 203, 246
See application file for complete search history.

(56) References Cited

U.S. PATENT DOCUMENTS

| | | | | |
|---|---|---|---|---|
| 4,447,141 | A * | 5/1984 | Eisenkraft | 351/237 |
| 5,206,671 | A * | 4/1993 | Eydelman et al. | 351/203 |
| 5,956,126 | A | 9/1999 | Cody | |
| 6,511,175 | B2 | 1/2003 | Hay et al. | |
| 6,692,481 | B2 | 2/2004 | Guerrero | |
| 6,912,301 | B1 | 6/2005 | Lin et al. | |
| 7,004,912 | B2 | 2/2006 | Polat | |
| 7,033,025 | B2 | 4/2006 | Winterbotham | |
| 7,033,026 | B2 | 4/2006 | Spector | |
| 7,367,671 | B2 | 5/2008 | Sabel | |
| 7,513,622 | B2 | 4/2009 | Khaderi | |
| 2008/0062338 | A1 | 3/2008 | Herzog et al. | |
| 2009/0109398 | A1* | 4/2009 | Ellenbogen | 351/203 |

OTHER PUBLICATIONS

Huang, Chang-Bing et al., "Broad bandwidth of perceptual learning in the visual system of adults with anisometropic amblyopia," PNAS, Mar. 11, 2008, pp. 4068-4073, vol. 105, No. 10, www.pnas.org/cgi/doi/10.1073/pnas.0800824105.

Xu, Pengjing et al., "Identify mechanisms of amblyopia in Gabor orientation identification with external noise," Vision Research, 2006, pp. 3748-3760, vol. 46, Elsevier Ltd.

Lu, Zhong-Lin et al., "Characterizing Observers Using External Noise and Observer Models: Assessing Internal Representations With External Noise," Psychological Review, 2008, pp. 44-82, vol. 115, No. 1, American Psychological Association.

Zhou, Yifeng et al., "Perceptual learning improves contrast sensitivity and visual acuity in adults with anisometropic amblyopia," Vision Research, 2006, pp. 739-750, vol. 46, Elsevier Ltd.

* cited by examiner

*Primary Examiner* — Jordan M. Schwartz
(74) *Attorney, Agent, or Firm* — Fulbright & Jaworski L.L.P.

(57) ABSTRACT

A vision treatment system comprises a computer and a user input output module associated with the computer, the user input output module including a display screen and means for receiving user input, wherein the computer includes a testing and training module for one or more vision disorders, the training and testing module in communication with the user input output module and testing a user's cutoff spatial frequency of a contrast sensitivity and applying a training regimen based upon Perceptual Template Model (PTM) analysis of interactions with the user.

28 Claims, 7 Drawing Sheets

VISION TREATMENT PROCEDURES AND DEVICES

TECHNICAL FIELD

The present description is related, generally, to treatment of vision disorders and, more specifically, to treatment of vision disorders using a Perceptual Template Model (PTM) analysis and interactive training.

BACKGROUND OF THE INVENTION

Amblyopia is commonly known as "lazy eye." It is a brain and nerve defect, rather than an eye defect, so it cannot be corrected by refractive means, such as lenses. Amblyopia is the most common cause of visual impairment in children and the leading cause of vision loss in one eye in the twenty to seventy year-old age group. Amblyopia has a high occurrence rate in many countries.

In amblyopes, both eyes are usually quite normal, but the neural pathway, from the visual cortex to the eyes, is not developed completely, so the visual cortex cannot see the information from the lazy eye. A primary symptom of amblyopia is a lack of contrast sensitivity. The traditional therapy for amblyopia is occlusion (i.e., patching the normal eye for lengthy periods). But there are significant disadvantages to using occlusion therapy. The first disadvantage is that occlusion therapy is distressing to children. The second disadvantage is that occlusion is often ineffective. One-third of the children using occlusion therapy gain little or even no visual benefit, and occlusion therapy is not effective for adults. Moreover, occlusion therapy can reduce a patient's stereo acuity while not treating the patient's lack of contrast sensitivity. Despite the disadvantages, occlusion therapy is still widely practiced.

BRIEF SUMMARY OF THE INVENTION

Various embodiments of the invention are directed to systems and methods for treating eye disorders through diagnosing a user's cutoff spatial frequency of a contrast sensitivity and selecting a training regimen based thereon. The training regimen is interactive and includes Perceptual Template Model (PTM) analysis of interactions with the user to gradually improve the user's contrast sensitivity, thereby ameliorating one or more vision disorders (e.g., amblyopia).

PTM analysis allows for direct diagnosis of a user's specific vision disorder mechanism. For example, some users experience increased internal additive noise, deficient perceptual template, increased multiplicative noise, or a combination thereof. PTM analysis of the user's cutoff spatial frequency of a contrast sensitivity gives an indication of the vision disorder mechanism and can be used to facilitate the selection of an appropriate treatment/training regimen. As the user participates in the therapy program, the user's progress can be ascertained through PTM as well, with subsequent treatment/training regimens selected as before. Accordingly, a user's treatment is tailored to the user's specific needs.

The program is interactive in various embodiments. For instance, a user is shown visual images, and in response the visual images, the user inputs information to the treatment system (e.g., information indicating an appearance of the image to the user). As the user studies image after image, the user's contrast sensitivity is expected in increase, while the amblyopia is expected to be ameliorated. The treatment system uses the user interaction to measure progress and to tailor further treatment based thereon.

One example embodiment is based on a Personal Computer (PC) or laptop. The treatment program is stored as a computer program that is executed by the computer. The computer includes a video converter that provides high-resolution monochromatic images to the user. The system may employ the computer's standard monitor or another monitor specially suited for the high-resolution output.

In another embodiment, the system includes a processor and a high-resolution display screen embedded in display goggles. The goggles may communicate with a separate computer system (e.g., a laptop computer) in order to download updates or additions to the training program.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 1:
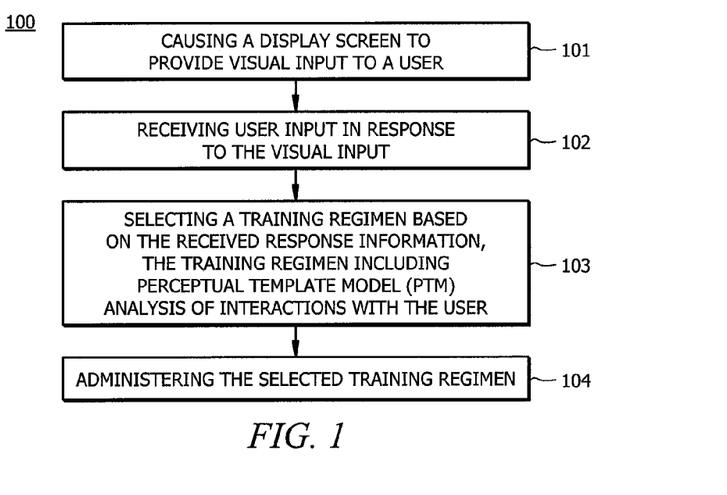
FIG. 1 is an illustration of an exemplary process, adapted according to one embodiment of the invention.

FIG. 1 is an illustration of exemplary process 100, adapted according to one embodiment of the invention. Process 100 is a technique for treatment of one or more vision disorders, including amblyopia, near sightedness (myopia), far sightedness, presbyopia, strabismus, hypermetropia, and the like. In block 101, a display screen provides visual input to a user (e.g., a patient undergoing therapy). For instance, in some embodiments, a computer screen, display goggles, or some other display screen renders one or more Gabor gratings with added external noise, internal noise, and increasing contrasts and noise variance across the screen. Gabor gratings are only one type of grating, and other types of gratings, or even non-grating visual input, can be rendered for a user. In fact, any type of visual input now known or later developed that can be used to indicate a user's cutoff spatial frequency of contrast sensitivity can be used in various embodiments.

In block 102, user input is received in response to the visual input. For instance, a user can employ any of a variety of input/output devices to interact with the vision treatment system including, e.g., a keyboard, joystick, keypad, game controller, motion detector, and the like. User responses to the input can provide an indication of user cutoff spatial frequency of contrast sensitivity, allowing for diagnosis of disorders and measurement of improvement. An example of a user response is input identifying an orientation of a particular grating.

In block 103, a training regimen is selected based on the received response information. Training can include, for example, showing the user a series of images that the user must respond to. Each of the images may be chosen, for instance, to cause the user to focus on visual images at or near the user's cutoff spatial frequency. In this example, the training regimen includes Perceptual Template Model (PTM) analysis of interactions with the user. Diagnosis of the user's disorder mechanism and severity is performed by analyzing the user's response to the visual input. For example, in the case of amblyopia, there are at least three different mechanisms—increased internal additive noise, deficient perceptual template, and increased multiplicative noise. Each of the three mechanisms can benefit from a different treatment regimen. Diagnosis and selection of the regimen is described in more detail below with respect to FIGS. 2 and 3.

In block 104, the selected training regimen is administered, e.g., using the display screen or another display screen (appropriate display screens are described in more detail below with respect to FIGS. 5-7). The regimen is interactive and provides visual input to the user. User responses to the input are analyzed using a PTM analysis to measure improvement. Based on the user responses, it is discerned which further visual input is appropriate for training. The regimen is applied until it is determined by a physician or the patient to stop treatment, e.g., after sufficient improvement of the visual disorder. In some embodiments, the training regimen may include, e.g., cartoons, music, sound effects, and the like to appeal to young children, and the content may be different from day to day to keep the children interested in the training. Furthermore, any of the embodiments shown herein can be adapted to include an entertainment function (e.g., compatibility with MP3 MPEG4 files) so that the device can be used as a multi-functional eye relaxing trainer.

Figure 2:
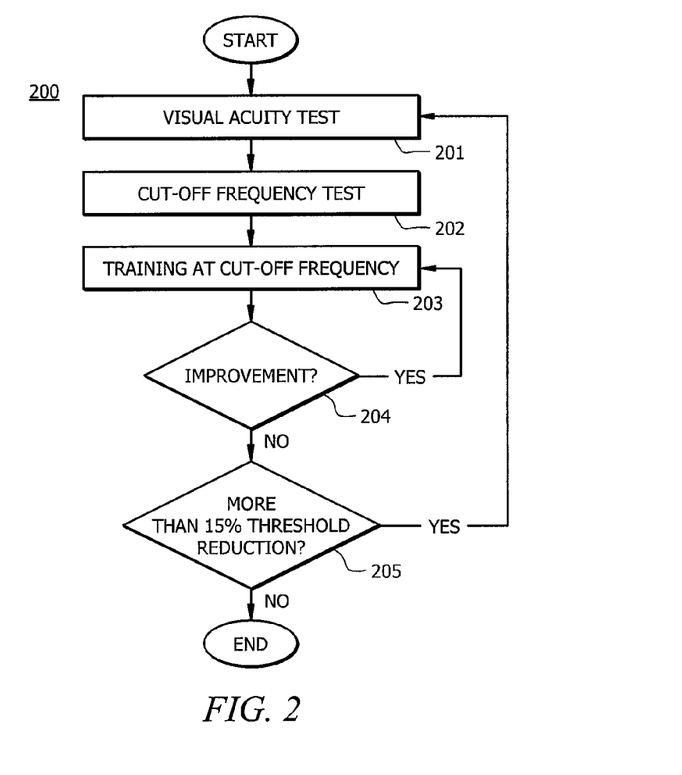
FIG. 2 is an illustration of an exemplary technique, adapted according to one embodiment of the invention for diagnosis and treatment of amblyopia.

FIG. 2 is an illustration of exemplary technique 200, adapted according to one embodiment of the invention for diagnosis and treatment of amblyopia. Technique 200 shows one instance of an application of process 100 (of FIG. 1).

In block 201, the user is given a visual acuity test. For example, the acuity test may include a computerized eye chart test. The acuity test can be performed at multiple times throughout treatment to provide a patient history record and facilitate assessment of the effectiveness of the training program. In block 202, the user is given a test to measure cut-off frequency of contrast sensitivity. In one example, a superposition of three images is created. The first image is a grating with increasing contrast in a vertical direction. The second image is an external noise image with increasing variance in the horizontal direction. The third image is a simulated internal noise image with constant variance. From the superposed image, an equal visibility contour is discerned, which denotes points within the superposed image where the user can begin to discern the grating. The elbow of the contour is an indicator of cut-off spatial frequency contrast sensitivity. Specifically, the amplitude of external noise at the elbow of the contour provides an estimate of the variance of the internal noise in the user's perceptual system. Block 202 can be used to diagnose the mechanism and severity of the user's visual disorder via, e.g., PTM analysis.

In block 203, training is performed at the cut-off frequency. For example, once the user's cut-off frequency of contrast sensitivity, mechanism, and severity, are known, treatment can be tailored to the individual. Treatment can include interactive sessions where the user detects gratings at or near the diagnosed cut-off spatial frequency.

In block 204, it is discerned whether the user shows improvement in response to the training. For example, further PTM analysis can be performed to provide an indication of cut-off frequency of contrast sensitivity once again. An improvement in cut-off frequency of contrast sensitivity can be followed up by a repeat of block 203 at a different cut-off frequency.

If there is no improvement in block 204, then it is discerned whether there has been a threshold reduction (e.g., by more or less than 15%). The contrast threshold is the minimum amount of stimulus energy that is required for a subject to detect the stimulus pattern. The stimulus energy is measured in terms of contrast—how much whiter or darker the stimulus is compared to the background. The smaller the threshold is, the more sensitive the user is. By measuring reductions of contrast threshold, it can be discerned how much the user improves in the training. In block 204 there is a check performed to discern whether there is 15% or more threshold decrease from the previous training session. If yes, the training is repeated at the same spatial frequency until there is less than 15% improvement. In block 205, a check is performed to discern whether the improvement at the current training spatial frequency is 15% or more lower than the starting threshold tested in block 202. If there has been a reduction in threshold of greater than 15%, then another visual acuity test is performed in block 201 and the whole training procedure will be repeated. If there is less than 15% threshold reduction, then the treatment is ended to, e.g., question the initial diagnosis of amblyopia or complete a successful treatment.

Figure 3:
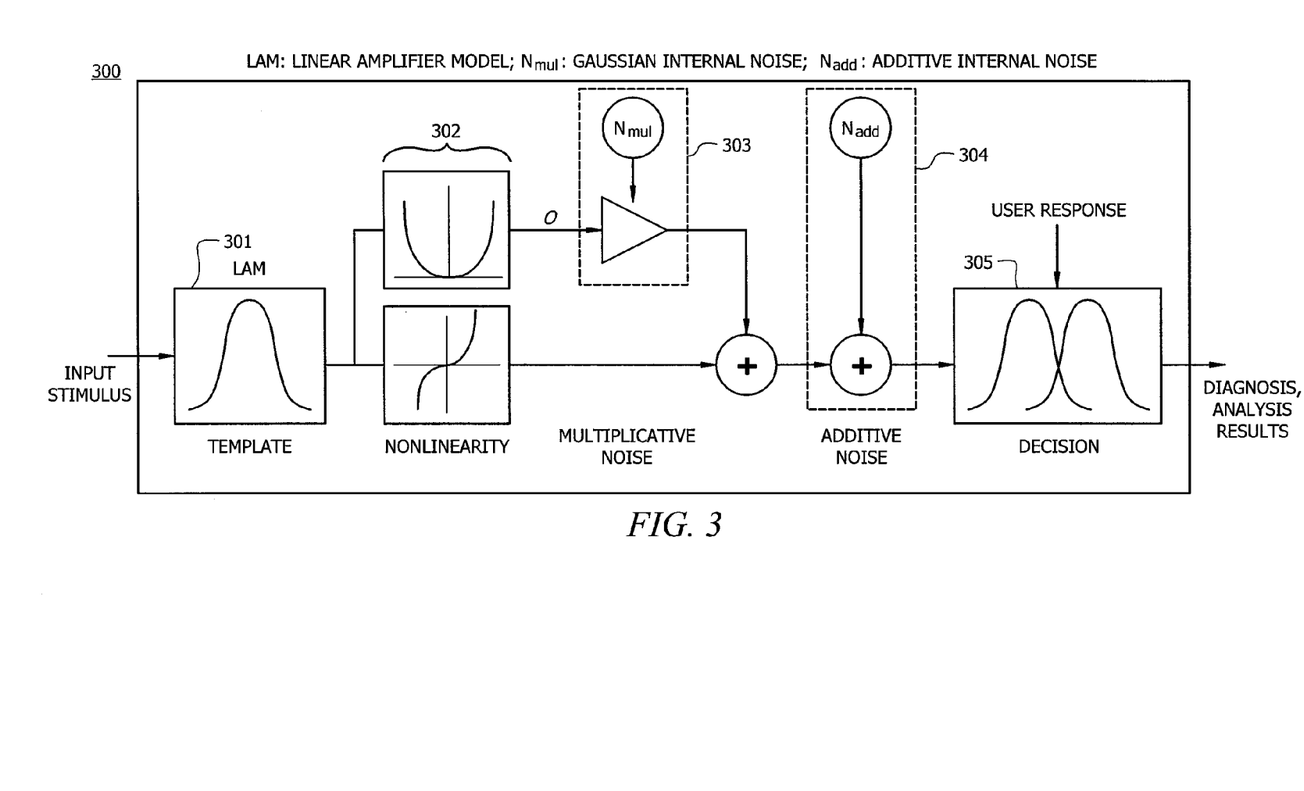
FIG. 3 is an illustration of an exemplary PTM analysis process according to an embodiment of the invention.

FIG. 3 is an illustration of exemplary PTM analysis process 300 according to an embodiment of the invention. Input stimulus (e.g., a grating) is received at block 301, which applies a Linear Amplified Model (LAM) perception template to the stimulus. The LAM perception template adds external noise to the input stimulus by, e.g., superimposing an image of external noise over the input stimulus. LAM techniques are explained in more detail in Xu et al., "Identify mechanisms of amblyopia in Gabor orientation identification with external noise," Vision Research 46 (2006) 3748-3760 (hereinafter, the "Xu paper"), the disclosure of which is hereby incorporated by reference in its entirety.

In block 302, a non-linear transducer function (e.g., power) is employed. The human visual system is a non-linear system (i.e., a system that does not satisfy the principle of superposition or a system whose output is not proportional to its input). The non-linearity of the human visual system can be modeled by transducer functions such that the output is a non-linear function of its input in sensory coding. The non-linear transducer function is a model of how the human brain works with stimulus and external and internal noise, based on the experimental data. The model can also be used to explain the mechanism underlying any improvement during training. In block 303, Gaussian internal noise is combined multiplicatively and additively. The Gaussian internal noise has a standard deviation that is proportional (with a factor of $N_{mul}$) to the total energy in the stimulus after the non-linear transformation.

In block 304, internal noise is added once again. The additive internal noise has an amplitude ($N_{add}$) that is independent of the stimulus strength. The modified visual stimulus then is shown to a user, and the user's response is input to processing unit 305, which performs analysis and diagnosis. In one example, the user's responses are input to an algorithm that provides a diagnosis of the mechanism and severity of the user's visual disorder. The Xu paper provides a description of analysis based on PTM.

One mathematical model used in PTM analysis is given in Equation 1, where $c\tau$ is a contrast threshold at a given performance criterion, $\tau$. The contrast threshold in Equation 1 is the theoretical contrast threshold predicted by the PTM model, which can be compared to empirically measured contrast thresholds of the user. Equation 1 relates the behaviorally measured contrast threshold with four parameters that characterize different properties of the human visual system. One parameter, $N_{ext}$, is variance of (experimenter-controlled) external noise, and d' is the signal to noise ratio. $N_{mul}$ is Gaussian multiplicative noise, which is proportional to the stimulus energy. $N_{add}$ is additive noise, which is independent of stimulus energy. Both multiplicative and additive internal noise characterize processing inefficiencies in the human visual system. Additive internal noise reflects the existence of an absolute threshold in the absence of external noise. The internal multiplicative noise that increases with input stimulus energy diminishes the benefit from increasing stimulus contrast, as shown by Weber's law. Equation 1 is used to explain the possible contrast threshold reduction of the user. For example, if $c\tau$ is reduced after training, it could indicate a reduction of $N_{add}$. Through repeated measurements, the mechanisms of visual system changes can be inferred, for example following training or after adaptation.

$$c_\tau = \frac{1}{\beta}\left[\frac{(1+N_{mul}^2)N_{ext}^{2\gamma}+N_{add}^2}{(1/d'^2-N_{mul}^2)}\right]^{\frac{1}{2\gamma}}$$ Equation 1

Figure 4:
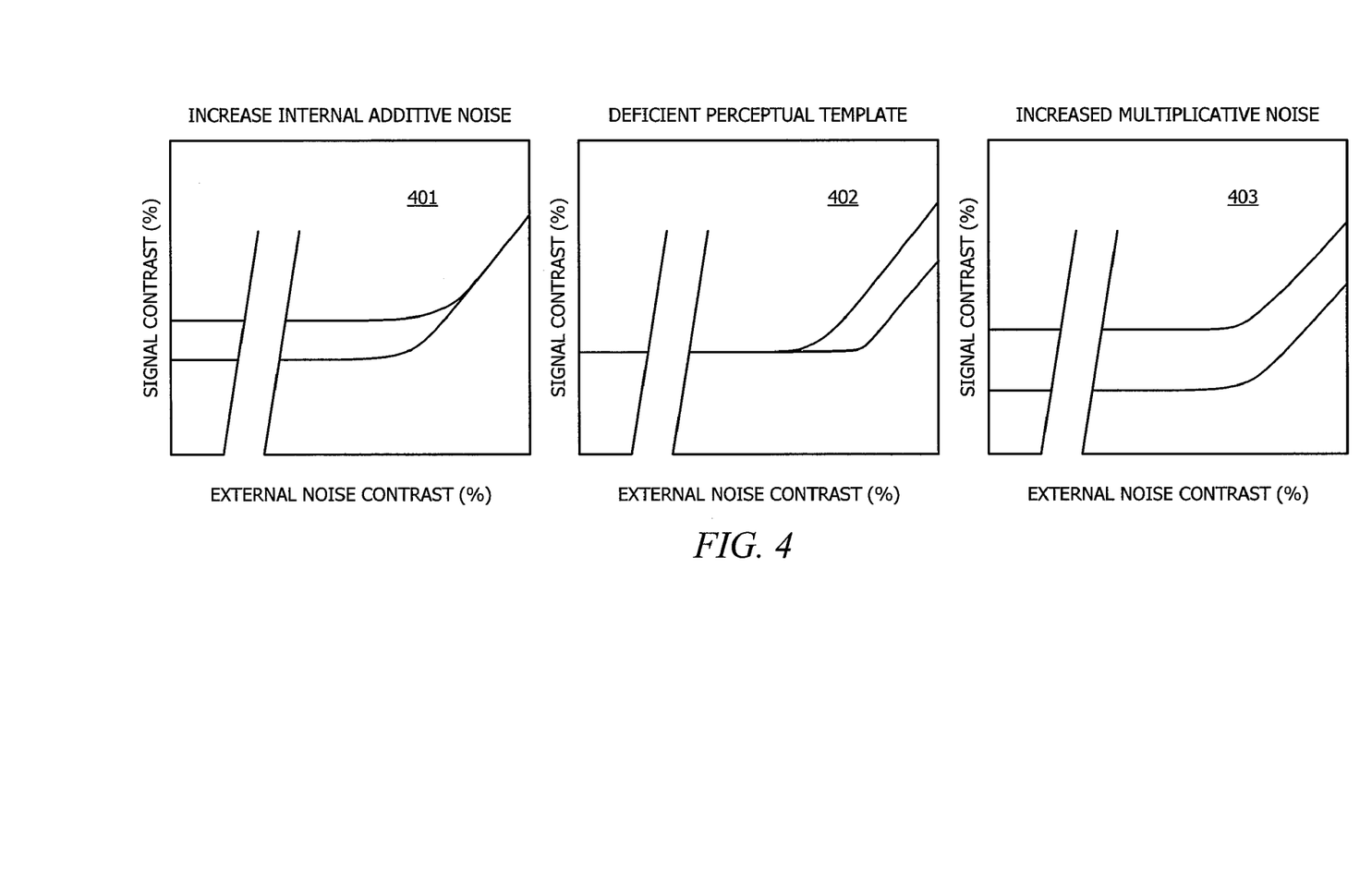
FIG. 4 is an illustration of graphs of prediction of three possible mechanisms of amblyopia by PTM analysis.

FIG. 4 is an illustration of graphs of predictions of three possible mechanisms of amblyopia. The curves shown are contrast thresholds as functions of external noise levels for one or more Gabor spatial frequencies. The oblique lines in each graph indicate where part of a curve is omitted because the curve does not change within a relatively large range. Graph 401 shows what a user's responses might look like if the user's amblyopia conforms to an increased internal additive noise mechanism. Graph 402 shows what a user's response might look like if the user's amblyopia conforms to a deficient perceptual template mechanism, and graph 403 shows what a user's response might look like if the user's amblyopia conforms to an increased multiplicative noise mechanism. However, individual responses are expected to show some amount of deviation from the graphs of FIG. 4, and it is also expected that some individuals may suffer from more than one mechanism of amblyopia. Processing unit 305 of FIG. 3 includes instructions, which when executed, cause processing unit 305 to analyze the user's responses against the various models, thereby transforming the user's responses into output that facilitates treatment. The output of processing unit 305 can include any of a variety of types of information, including, e.g., an indication of mechanism, a graph, raw data, derived data, proposed training regimens, any combination thereof, and the like.

Figure 5:
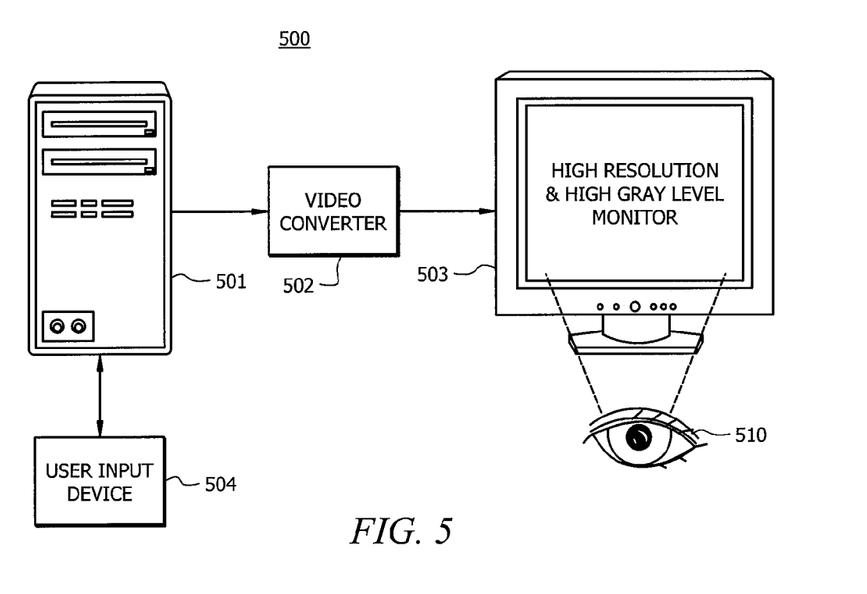
FIG. 5 is an illustration of an exemplary system, adapted according to one embodiment of the invention.

FIG. 5 is an illustration of exemplary system 500, adapted according to one embodiment of the invention. System 500 is one embodiment of a vision treatment device and can be employed to perform the exemplary processes of FIGS. 1 and 2. System 500 includes Personal Computer (PC) 501, video converter 502, monitor 503, and user input device 504. PTM analysis and other processing is performed by PC 501. In this example, PC 501 executes code to provide the functionality of the interactive training program. In any of the embodiments, the computer-executable code may be stored to any of a variety of computer-readable storage devices, such as a hard drive media, optical media, RAM, EPROM, EEPROM, tape media, cartridge media, flash memory, ROM, memory stick, and/or the like. In fact, readable media can include any medium that can store information. Monitor 503 displays the training visual input to user 510, who responds to the training visual input via user input device 504 (e.g., a keyboard, joystick, etc.).

Video converter 502, in this embodiment, includes capabilities above and beyond that of conventional video converters. For instance, video converter 502 is capable of providing a high-resolution monochromatic display on twelve or more bits. An exemplary video converter is described in more detail with respect to FIG. 6. Monitor 503 is capable of displaying a monochromatic image according to its full number of bits (e.g., twelve bits or more). Conventional Liquid Crystal Displays (LCDs) are capable of providing 10-14 bits output, and those providing twelve bits or better can be adapted for use in system 500. Cathode Ray Tube (CRT) monitors can provide twelve or more bits of monochromatic resolution but may be too large or heavy for some uses. Any monitor type now known or later developed capable of providing a satisfactory bit resolution in a monochromatic image can be adapted for use in various embodiments.

While the embodiment of FIG. 5 shows a PC, it should be noted that any processor-based device with adequate processing capability and adequate input/output compatibility can be used in various embodiments. Furthermore, video converter 502 can be implemented in hardware, software, or a combination of the two.

Figure 6:
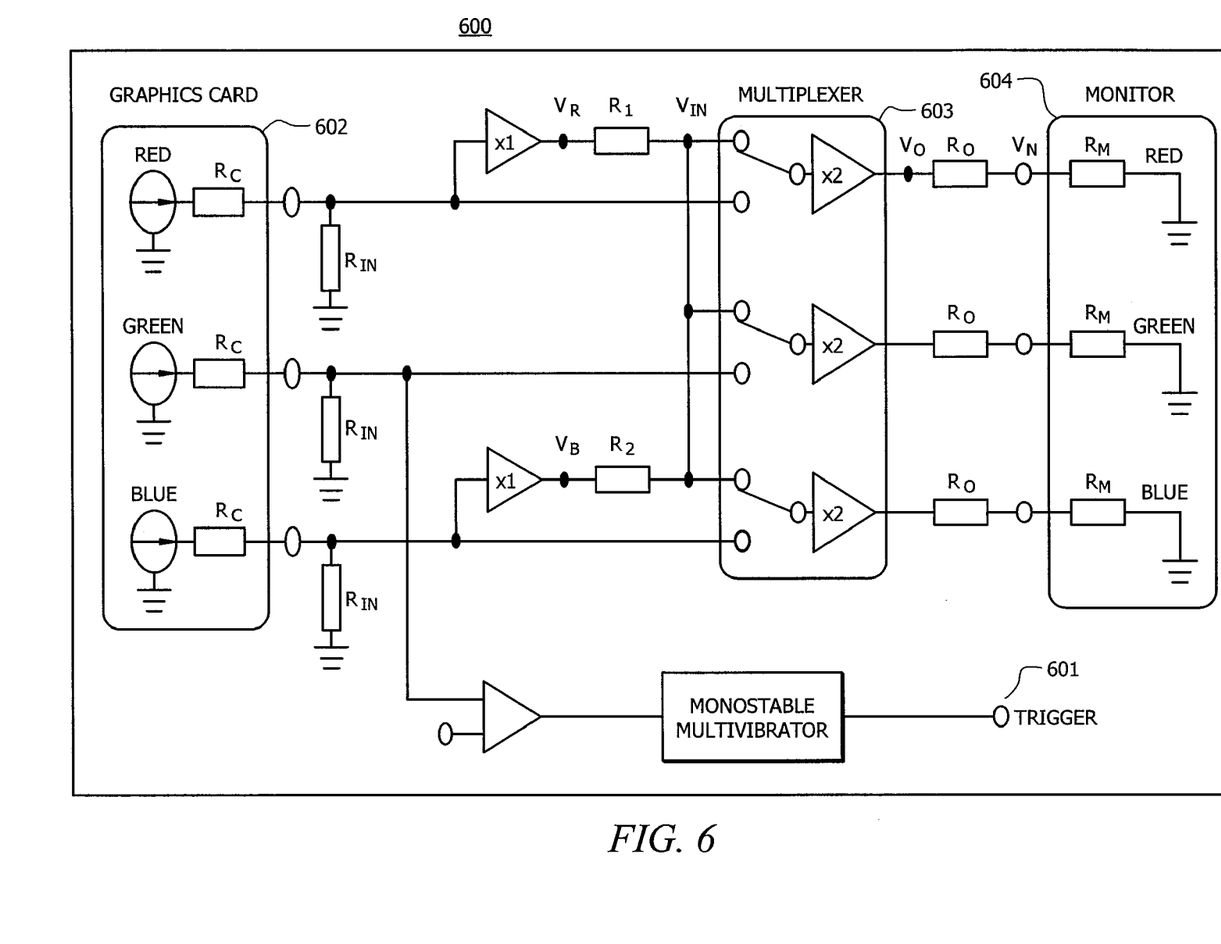
FIG. 6 is an illustration of an exemplary video converter, adapted according to one embodiment of the invention.

FIG. 6 is an illustration of exemplary video converter 600, adapted according to one embodiment of the invention. Video converter 600 can be used in system 500 (FIG. 5) and can provide fourteen bits of monochromatic resolution for real time medical imaging. Conventional video converters can provide only 24 bits in three colors, which gives eight bits monochromatic. Video converter 600 provides 12-14 bits monochromatic, giving significant visual resolution to the amblyopia patient and facilitating the display of complex training visual input.

Video converter 600 includes trigger 601, graphics card 602, multiplexor 603, and monitor 604. Multiplexor 603 and monitor 604 only use two of the three channels, Red (R) and Blue (B), and use R and B as a single channel for high resolution display. G, the green channel, is used for synchronization with, e.g., the visual display card in medical imaging instrument, such as a functional MRI or diffusion tensor imaging system.

Video converter 600 utilizes video attenuator techniques to generate a single-channel high resolution display from the R and B outputs of the graphics, and duplicates the same signal to drive the three RGB channels of color monitors. The Blue-to-Red Ratio (BTRR) is R1/R2, where R1 and R2 are resistor values. Voltage at the monitor input (VM) is given by Equation 2. Thus, if R1 is 150 ohms and R2 is 3.6 ohms, then BTRR is 41.67, which gives approximately fourteen bits.

$$Vm = Vin = 1/(BTRR+1)V_R + BTRR/(BTRR+1)V_R \quad \text{Equation 2}$$

Video converter 600 operates as an adaptor to couple a convention video-out of a computer to color monitor 604 to provide twelve or more bits of monochromatic resolution. FIG. 6 shows video converter 600 in hardware. However, various embodiments of the invention implement various functionality in software or a mixture of software and hardware.

Figure 7:
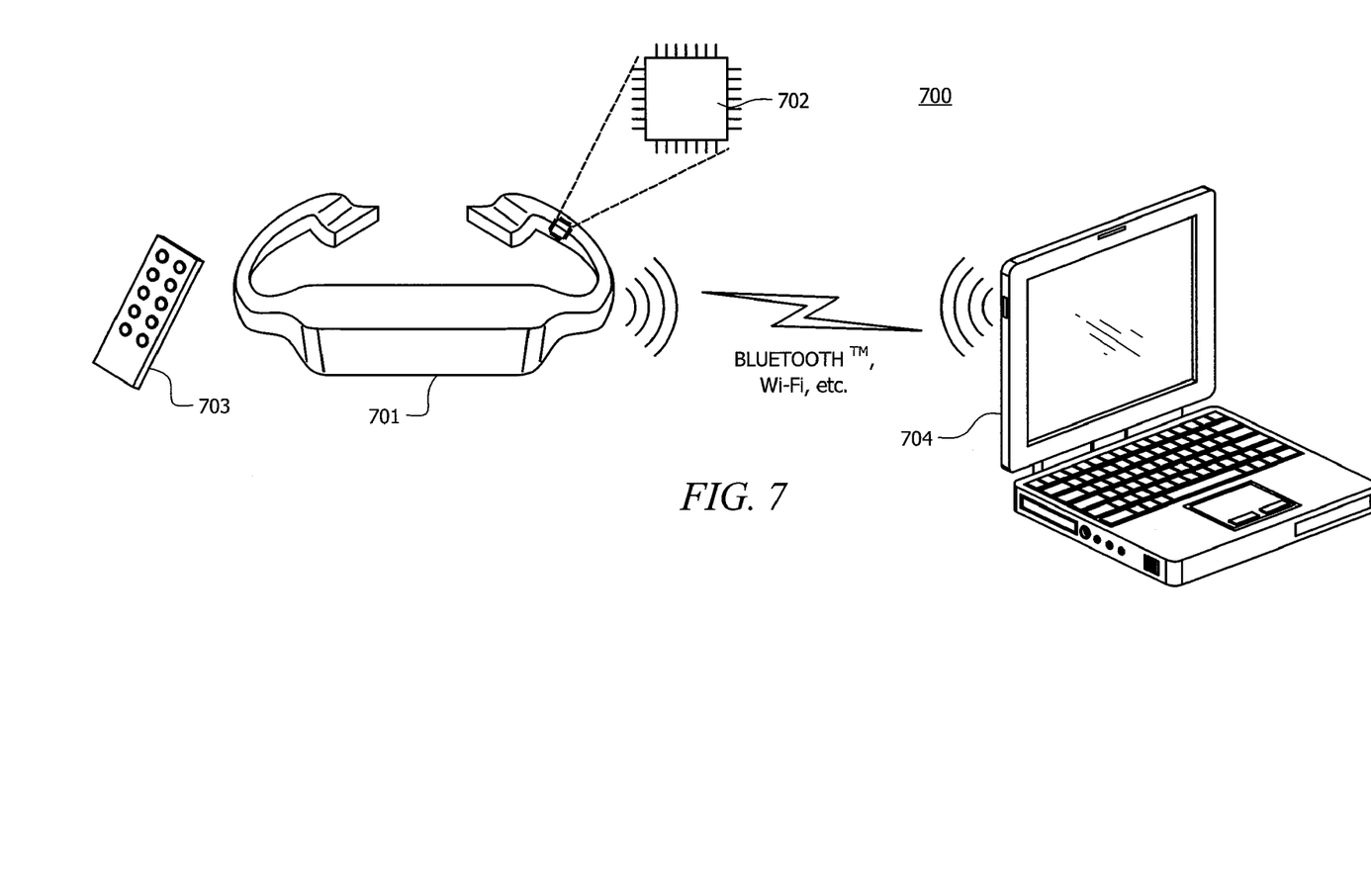
FIG. 7 is an illustration of an exemplary system, adapted according to one embodiment of the invention.

FIG. 7 is an illustration of exemplary system 700, adapted according to one embodiment of the invention. System 700 includes display goggle 701, which has reprogrammable processor 702, user input device 703, and laptop computer 704.

Processor 702 accesses computer-executable code from internal or external storage. When the code is executed, the processor provides the functionality of the interactive training program. Any of a variety of microprocessors can be used, including general-purpose processors, microcontroller units (MCUs), Field Programmable Gate Arrays (FPGAs), Application-Specific Integrated Circuits (ASICs), and the like. Processor 702 includes re-programmability, which allows it to receive and implement modifications to the interactive training program, for example, to update a user's training regimen and/or to treat other visual disorders, such as strabismus. Video conversion may be implemented by processor 702 or another functional unit to provide 12-14 bits of monochromatic resolution on an LCD display (not shown) within goggle 701.

Goggle 701 communicates with computer 704 wirelessly (or even by wire in some embodiments). The communication between computer 704 and goggle 701 can be used to update the interactive training program, to report results to a physician via the Internet, to assist in processing, and/or the like. The embodiment of FIG. 7 offers a user the advantage of portability.

Figure 8:
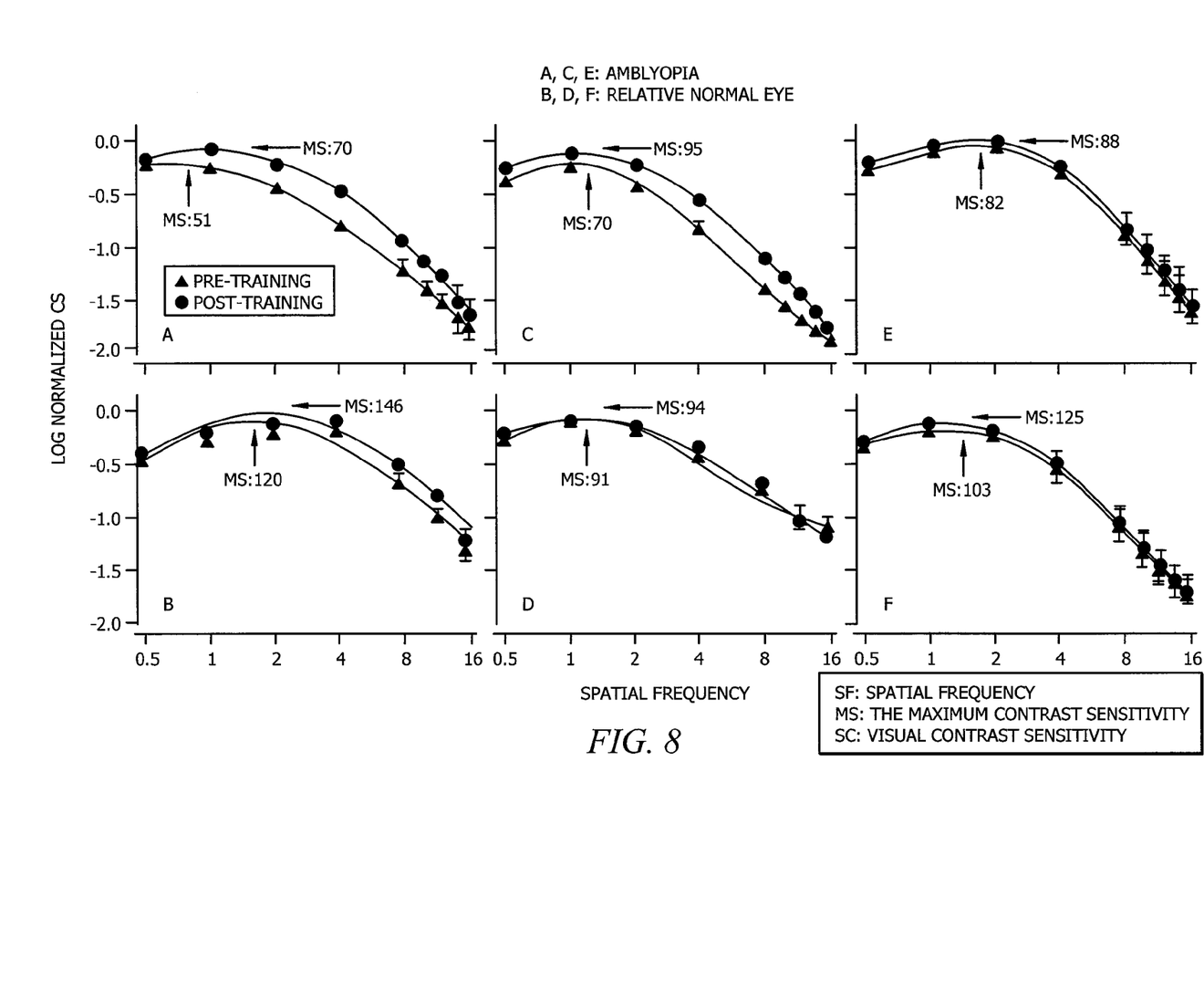
FIG. 8 is an illustration of results of testing of one embodiment of the invention that performs the processes of FIGS. 1 and 2.

FIG. 8 is an illustration of results of testing of one embodiment of the invention that performs the processes of FIGS. 1 and 2. There are six graphs, and three groups of patients. Graphs A, C, and E are results for amblyopia patients. Graphs B, D, and F are from normal subjects. Graphs E and F are the control subjects who did not participate in the interactive training program. The x-axis is spatial frequency, the y-axis is log normalized visual contrast sensitivity, and the curves show average maximum contrast sensitivity for the respective groups.

Graphs A and B are the results from a group of subjects at the ages of seven and eight, and the spatial frequency is 0.5. As shown in graph A, after treatment, the average maximum contrast sensitivity of the amblyopia patients increased from 51 to 70. As shown in graph B, even the patients with relatively normal eyes had an increase in maximum contrast sensitivity.

Graphs C and D show the results of another group at the age of ten years old and with nine different spatial frequencies. As shown in graph C, after treatment, the maximum contrast sensitivity increased to 95 for amblyopia patients and also increased for non-amblyopia patients in graph D.

Furthermore, while not shown in FIG. 8, visual acuity increased for the patients who used the interactive training. Before training average acuity was only 0.18 for the groups. After training, the average visual acuity improved to 0.29.

Various embodiments of the invention stand in contrast to current systems and techniques in use in various countries around the world to treat amblyopia. Table 1 shows a comparison of the features of some current systems. It is notable that only the NeuroVision system from Singapore provides an interactive training regimen; however, the NeuroVision system uses only LAM analysis, which is not as robust as the PTM analysis used by various embodiments of the present invention at least because LAM analysis does not model internal noise. Additionally, Ruiseng New Vision Co. Ltd, Xi-An Jiaotong University, Guangzhou Eyeabc Medical And Health-care Research Institute, Xi-An Huaya Electronics Company, Guangzhou Shi-Jia photoelectronic Company, Guangdong Medical Instruments Institute, and Hangzhou Huatai Medical Instruments Company have embarked on programs to treat amblyopia in China, but such systems and techniques are passive and do not use PTM or LAM analysis.

TABLE 1

| Company | Country | Model Name | Working Principle | Disadvantages |
|---|---|---|---|---|
| OOEED Distribution Network | China | Laser eye exercise device | Exercise designed Laser | Passive Children only |
| OphthoCare | Israel | LCG (Liquid Crystal Glasses) | Electronic shutter incorporated into optical refractive lens | Passive; Children only |
| Eyerobics | Australia | Eyerobics program in a DVD | Video or DVD filled with simple eye exercises | Passive; Children only |
| NeuroVision | Singapore | NeuroVision treatment | A series of computerized visual tasks which enhance visual part of brain to better process vision | Available at clinic only - not portable |
| Zhuzhou Huaming Eye Healthcare Instrument Factory | China | WenHui Model DT-F2 amblyopia treatment instrument | Utilizing digital circuit & analog circuit, instrument generates modulating differential pulse of high frequency & low frequency | Passive; Children only |
| OOEED Distribution Network | China | Laser eye exercise device | Exercise designed Laser | Passive; Children only |
| OphthoCare | Israel | LCG (Liquid Crystal Glasses) | Electronic shutter incorporated into optical refractive lens | Passive; Children only |

Various embodiments include advantages over prior art techniques. For instance, many prior art techniques use a passive, one-size-fits-all training regimen, which is less effective than the regimens administered by embodiments of the present invention that are customized to a user's particular diagnosis. Furthermore, while various techniques in the past have utilized LAM analysis, such LAM analysis is not as robust as PTM analysis. Specifically, LAM analysis lacks a stimulus-dependent internal noise model and cannot adequately model slopes of psychometric functions. Examples of psychometric functions include the curves shown in FIG. 4. As a result, PTM analysis: 1) provides a better account of threshold versus contrast functions at multiple performance levels and psychometric functions, 2) uses internal noise to better identify amblyopic mechanisms, and 3) accommodates independent mechanisms of amblyopia at high and low external noise levels. Furthermore, training focused on contrast sensitivity tends to be much more robust and effective, even across all age levels, than techniques using occlusion. Additionally, various embodiments utilizing PCs, laptop computers, and/or goggles offer flexibility of location. In other words, such embodiments can be conveniently used at home or at a physician's office, and some embodiments are portable.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A computer program product having a computer readable medium having computer program logic recorded thereon for analyzing and treating one or more vision disorders, said computer program product comprising:
    code for causing a display screen to provide visual input to a user;
    code for receiving response information from the user based on the visual input, the response information comprising an indication of a cutoff spatial frequency of a contrast sensitivity of the user;
    code for selecting a training regimen based on the received response information, the training regimen including Perceptual Template Model (PTM) analysis of interactions with the user; and
    code for administering the selected training regimen.

2. The computer program product of claim 1 wherein the training regimen enhances the user's contrast sensitivity.

3. The computer program product of claim 1 wherein the training regimen detects the user's response to one or more gratings at the cutoff spatial frequency.

4. The computer program product of claim 1 wherein the code for selecting the training regimen uses the received response information to classify a mechanism of amblyopia, the mechanism selected from the list consisting of:
    increased internal additive noise;
    deficient perceptual template; and
    increased multiplicative noise.

5. The computer program product of claim 1 wherein the code for causing the display screen to provide visual input comprises:
    code for rendering a superimposed image, the superimposed image comprising:
        a grating with increasing contrast in a vertical direction;
        an external noise image with increasing variance in a horizontal direction; and
        a simulated internal noise image with a constant variance.

6. The computer program product of claim 5 wherein the received response information comprises:
    a user response indicating an orientation of the grating.

7. The computer program product of claim 1 further comprising:
    code for downloading training regimen updates.

8. The computer program product of claim 1 further comprising:
    code for transforming a video signal to provide the visual input with at least twelve bits of monochromatic resolution.

9. The computer program product of claim 1 wherein the code for administering the selected training regimen includes:
    code for receiving input stimulus and applying a Linear Amplified Model (LAM) perceptual template to the input stimulus to create a first signal;
    code for applying nonlinearity and multiplicative noise to the first signal to create a second signal;
    code for applying additive internal noise to the second signal to create a third signal;
    code for rendering an image to the user employing the third signal;
    code for receiving user input in response to the image; and
    code for analyzing the user input to tailor the training program according to the user input.

10. The computer program product of claim 1, wherein the code for administering the selected training regimen includes:
    code for presenting one or more of cartoons, music, and sound effects.

11. The computer program product of claim 10, wherein the code for presenting one or more of cartoons, music, and sound effects includes:
    code for presenting different material day-to-day.

12. A system comprising:
    a processor; and
    a user input output assembly associated with the processor, the user input output assembly including a display screen and means for receiving user input;
    wherein the processor executes a testing and training module for one or more vision disorders, the training and testing module in communication with the user input output assembly and testing a user's cutoff spatial frequency of a contrast sensitivity and applying a training regimen based upon Perceptual Template Model (PTM) analysis of interactions with the user.

13. The system of claim 12 wherein the user input output assembly comprises:
    goggles; and
    a keypad.

14. The system of claim 13 wherein the goggles comprise a wireless communication module to download training software.

15. The system of claim 12 wherein the display screen comprises:
   a computer Liquid Crystal Display (LCD) monitor.

16. The system of claim 12 further comprising:
   a video converter providing at least 12 bits of monochromatic imaging.

17. The system of claim 12 wherein the system further comprises:
   a synchronizing output compatible with medical imaging equipment.

18. The system of claim 12 wherein the processor is embodied in a Personal Computer (PC), and the user input output assembly comprises peripherals associated with the PC.

19. The system of claim 18 further comprising a video converter receiving video output signals from the PC, providing at least twelve bits of monochromatic resolution to the video signal, and passing the video signal to the display screen.

20. The system of claim 12 wherein the processor comprises one or more of an Application Specific Integrated Circuit (ASIC), a Microcontroller unit (MCU), and a Field Programmable Gate Array (FPGA).

21. A system for treating amblyopia, the system comprising:
   means for rendering a visual image to a user;
   means for receiving user information in response to the visual image, the user information comprising an indication of a contrast sensitivity of the user; and
   means for diagnosing a mechanism of amblyopia of the user and selecting an interactive training regimen for the user in accordance with Perceptual Template Model (PTM) analysis of the received user information.

22. The system of claim 21 wherein the visual image comprises:
   a grating, internal noise, and external noise.

23. The system of claim 21 wherein the PTM analysis comprises:
   examining the received user information to diagnose a mechanism of the amblyopia; and
   during the course of the training regimen, receiving subsequent user information and measuring user improvement based thereon.

24. The system of claim 21 wherein the means for rendering a visual image to a user includes an item selected from the list consisting of:
   a Liquid Crystal Display (LCD) screen embedded in goggles; and
   an LCD screen associated with a PC.

25. The system of claim 21 wherein the means for rendering a visual image to a user comprises:
   a video converter receiving a first image signal and transforming the first image signal to include at least 12 bits of monochromatic resolution.

26. The system of claim 21 wherein the means for receiving user information are selected from the list consisting of:
   a keyboard;
   a joystick; and
   a keypad.

27. The system of claim 21 wherein the means for diagnosing a mechanism of amblyopia of the user and selecting an interactive training regimen includes an item selected from the list consisting of:
   an Application Specific Integrated Circuit;
   a Microcontroller Unit (MCU); and
   a reprogrammable processor.

28. The system of claim 21 further adapted to treat one or more of strabismus, presbyopia, myopia, and hypermetropia.

* * * * *

UNITED STATES PATENT AND TRADEMARK OFFICE
CERTIFICATE OF CORRECTION

| | | |
|---|---|---|
| PATENT NO. | : 8,002,409 B2 | Page 1 of 1 |
| APPLICATION NO. | : 12/502517 | |
| DATED | : August 23, 2011 | |
| INVENTOR(S) | : Geng Li et al. | |

It is certified that error appears in the above-identified patent and that said Letters Patent is hereby corrected as shown below:

On the Title Page

Item 73, Assignee (left hand column), delete the portion of text reading "Hon Kong" and replace with --Hong Kong--.

Signed and Sealed this
Fourth Day of October, 2011

David J. Kappos
*Director of the United States Patent and Trademark Office*